United States Patent
Breitscheidel et al.

(10) Patent No.: US 6,313,358 B1
(45) Date of Patent: Nov. 6, 2001

(54) METHOD FOR PRODUCING HEXANEDIOL

(75) Inventors: Boris Breitscheidel, Limburgerhof; Rolf Pinkos; Frank Stein, both of Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,125

(22) PCT Filed: Apr. 12, 1999

(86) PCT No.: PCT/EP99/02448

§ 371 Date: Oct. 11, 2000

§ 102(e) Date: Oct. 11, 2000

(87) PCT Pub. No.: WO99/55653

PCT Pub. Date: Nov. 4, 1999

(30) Foreign Application Priority Data

Apr. 23, 1998 (DE) .............................. 198 18 096

(51) Int. Cl.$^7$ .......................... C07C 27/00; C07C 31/18; C07C 27/26
(52) U.S. Cl. .......................... 568/864; 568/861; 568/852; 568/868; 560/191
(58) Field of Search .................. 568/852, 861, 568/864, 868; 560/191

(56) References Cited

U.S. PATENT DOCUMENTS 5,403,962  4/1995  Schneider .
5,614,644  3/1997  Liang .
6,008,418 * 12/1999  Baur et al. ............................ 568/853

FOREIGN PATENT DOCUMENTS 522 463     4/1996  (EP) .
97/31882    9/1997  (WO) .

OTHER PUBLICATIONS

Houben Weyl, Meth.der Org.Chem.,vol. IV/1c, 1980 pp. 45–67.

Houben Weyl, Meth.derOrg.Chem.,vol. IV/1c, 1980 pp. 16–26.

* cited by examiner

Primary Examiner—Samuel Barts
Assistant Examiner—Elvis O. Price
(74) Attorney, Agent, or Firm—Keil & Weinkauf

(57) ABSTRACT

Hexanediol is prepared by hydrogenating dialkyl adipates or mixtures which contain a dialkyl adipate as the essential component and organic halogen compounds as impurities, by a process in which, before the hydrogenation, the dialkyl adipates or the mixtures containing dialkyl adipates are passed at from 50 to 250° C. and from 1 to 100 bar over copper catalysts which have a copper content, calculated as CuO, of from 0.5 to 80% by weight, a surface area of from 5 to 1500 m$^2$/g, a porosity of from 0.05 to 1.5 cm$^3$/g and a copper surface area of from 0.1 to 20 m$^2$/g, in order to remove the organic halogen compounds.

10 Claims, 1 Drawing Sheet

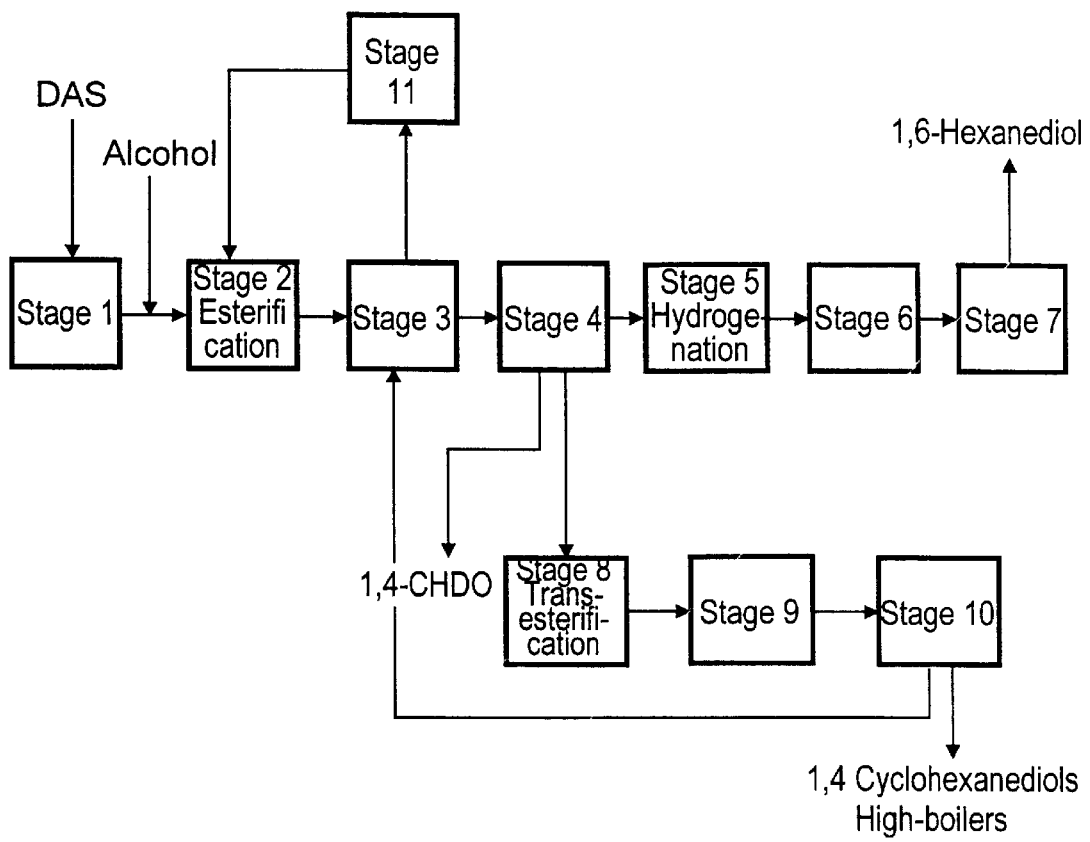

METHOD FOR PRODUCING HEXANEDIOL

This is the National stage of PCT/EP99/02448, filed Apr. 12, 1999.

The present invention relates to a process for the preparation of 1,6-hexanediol by hydrogenating adipic esters or ester mixtures which contain these and which contain organic halogen compounds as an impurity, the starting material being passed over a copper catalyst to remove the halogen compounds before the hydrogenation.

WO 97/31 882 describes a process for the preparation of 1,6-hexanediol in which a carboxylic acid mixture which contains essentially adipic acid and 6-hydroxycaproic acid and is obtained as a byproduct of the oxidation of cyclohexanone/cyclohexanol with oxygen or oxygen-containing gases and by water extraction of the reaction mixture is esterified with a low molecular weight alcohol to give the corresponding carboxylic esters, and the esterification mixture obtained is freed from excess alcohol and low boilers in a first distillation stage, the separation of the bottom product into an ester fraction essentially free of 1,4-cyclohexanediols and a fraction containing at least the major part of the 1,4-cyclohexanediols being carried out in a second distillation stage and the ester fraction essentially free of 1,4-cyclohexanediols being catalytically hydrogenated.

It has now been found that the activity of the hydrogenation catalyst decreases in the course of time, and it is presumed that this deactivation is attributable to the content of organic halogen compounds in the starting material.

It is an object of the present invention to remove these organic halogen compounds completely or virtually completely, i.e. to a residual content of less than 0.5 ppm, preferably less than 0.1 ppm.

The removal of organic halogen impurities from another substrate is known. For example, U.S. Pat. No. 5,614,644 describes the removal of organic halogen compounds from furan and hydrogenated furan using copper-containing catalysts. There, however, it is possible only to reduce the content of the impurity from 50–2000 ppm to less than 15 ppm, preferably to less than 5 ppm.

We have found that this object is achieved and that surprisingly, in a process for the preparation of hexanediol by hydrogenating dialkyl adipates or mixtures which contain a dialkyl adipate as the essential component and organic halogen compounds as impurities, it is possible to reduce the content of organic halogen compounds to extremely low values, for example less then 0.5 ppm, preferably less than 0.1 ppm, and hence greatly to increase the time on stream of the hydrogenation catalyst if, before the hydrogenation, the dialkyl adipates or the mixtures containing dialkyl adipates are passed, preferably in the liquid phase, at from 50 to 250° C. and from 1 to 100 bar over copper catalysts which have a copper content, calculated as CuO, of from 0.5 to 80% by weight, a surface area of from 5 to 1500 m²/g, a porosity of from 0.05 to 1.5 cm³/g and a copper surface area of from 0.1 to 20 m²/g (in each case per g of catalyst), in order to remove the organic halogen compounds.

With the copper catalysts to be used according to the invention, not only is it possible virtually completely to remove the halogen compounds but they are furthermore distinguished by the fact that they are chemically stable with respect to the ester mixture, i.e. no catalyst components can be detected in the ester mixture freed from the halogen-containing impurities and, apart from the removal of the halogen-containing impurities, they do not change the ester mixture chemically in its composition.

It is assumed that, in the treatment of the starting material stream with the copper catalysts, cleavage of the organic halogen compounds occurs and the copper catalysts simultaneously serve as absorbents for the liberated halogens. The terms catalyst and absorbent are therefore used synonymously below.

Both unsupported and supported copper catalysts can be used as copper-containing halogen absorbents.

On the one hand, supported copper catalysts in which the copper component is present in finely divided form on an inert carrier are preferably used. Examples of suitable carriers are active carbons, silicon carbide, alumina, silica, titanium dioxide, zirconium dioxide, zink oxide, magnesium oxide, calcium oxide, barium sulfate or mixtures thereof, preferably active carbons and zirconium dioxide. The carriers can be used, for example, in the form of extrudates, pellets, tablets or granules.

On the other hand, unsupported copper catalysts which contain, for example, $TiO_2$, $Al_2O_3$, $ZrO_2$ or mixtures of these compounds, among these preferably $TiO_2$, as further components in addition to copper are preferably used.

The catalysts to be used according to the invention have a copper content, calculated as CuO, of 0.5–80, preferably 2–60, % by weight, a surface area of 5–1500, preferably 10–1000, m²/g and a porosity of 0.05–1.5, preferably 0.1–0.8, cm³/g.

Particularly preferably used supported catalysts are on the one hand $ZrO_2$-supported copper catalysts which have a copper content, calculated as CuO, of 2–8% by weight, a surface area of 50–150 m²/g, a porosity of 0.2–0.4 cm³/g and a copper surface area of 1.0–3.0 m²/g and, on the other hand, active carbon-supported copper catalysts which have a copper content, calculated as CuO, of 2–8% by weight, a surface area of 500–1000 m²/g, a porosity of 0.5–0.8 cm³/g and a copper surface area of 1.0–5.0 m²/g.

Particularly preferably used unsupported catalysts are unsupported copper catalysts which contain $TiO_2$ as a further component in addition to copper and have a copper content, calculated as CuO, of 20–60% by weight, a surface area of 10–150 m²/g, a porosity of 0.1–0.5 cm³/g and a specific surface area of 0.5–3.0 m²/g.

The catalysts to be used according to the process are distinguished in particular by a large copper surface area of 0.1–20.0, preferably 0.5–10.0, particularly preferably 1.0–5.0, m²/g of catalyst. A large copper surface area is important for efficient removal of the halogen-containing impurities from the ester mixture and for a high absorption capacity of the copper-containing absorbent for the halogens eliminated. The specific copper surface area specified according to the claim is determined with the aid of $N_2O$ pulse chemisorption explained in more detail below.

Apparatus:

PulseChemiSorb 2705 from Micromeritics.

Sample Pretreatment:

About 0.3 g of reduced catalyst is placed in a quartz U-tube reactor with a broad sample part ($d_a$–11 mm). The sample is heated in a stream of 5% $H_2$/Ar (30 ml/min) at a heating rate of 5 K/min to 240° C. This is followed by reduction with hydrogen at 240° C. for two hours. The sample is then eluted for 30 minutes in a helium stream of 30 ml/min and cooled to 70° C. under this gas.

Carrying out the Measurement:

To measure the reactive $N_2O$ chemisorption, $N_2O$ pulses are metered into a helium stream of 30 ml/min by means of a metering loop (volume 1000 µl) and passed through the sample at 70° C. The pulsing is continued until four equal pulses (the same amount of $N_2O$ in each case) are detected in succession. The analysis of the amount of $N_2O$ consumed or of the $N_2$ formed is carried out on a short chromatographic separation column downstream of the reactor and containing Porapale-N® by means of a thermal conductivity detector.

Evaluation of the Measurement:

1. A mean value of the pulse area (MPA) in arbitrary units [a.U.] is determined from the constancy of four pulses each having the area content $PA^i$. With a total of n pulses, i.e.

$$MPA = \sum_{i=n-3}^{n} PA^i / 4 \quad (1)$$

From this MPA value, it is possible to convert the pulse areas into $\mu l$ with the aid of the reference volume RV.

$$xMPA\ [a.U.] = yRV\ [\mu l] \quad (2)$$

2. The amount of adsorbed gas AdG is calculated from the area content of the n individual pulses $PF^i$ as follows:

$$AdG[\text{w.E.}] = n * MPA - \sum_{i=1}^{n} PA^i = (n-4) * MPA - \sum_{i=1}^{n-4} PA^i \quad (3)$$

3. The amount of adsorbed gas AdG in $\mu l$ is calculated with the aid of (2).
4. The amount of adsorbed gas AdG [$\mu l$] is converted to standard conditions $AdG^S$ [$\mu l$].

$$AdG^S = AdG * \frac{273 * p^m}{760 * T^m} \quad (4)$$

$p^m$: pressure [mmHg]; $T^m$: adsorption temperature [K]
$p^m$ and $T^m$ are input as parameters before the measurement.

5. From $AdG^s$, the specific adsorbed amount of gas $V_m$ [$cm^3/g$] is calculated by standardization to the sample weight W.

$$V_m[cm^3/g] = \frac{AdG^{s[\mu l]}}{1000 * G[g]} \quad (5)$$

6. Calculation of $V_m$ in [mmol/g]

$$V_m[\mu mol/g] = 44.940 * V_m[cm^3/g] \quad (6)$$

7. Calculation of the specific copper surface area $S^m$ [$m^2/g^{Cat}$]:

$$S^m[m^2/g^{cat}] = \frac{V_m[\mu mol/g] * S * N_1 * 10^{-6}}{K} \quad (7)$$

S: Stoichiometry factor (assuming Cu=2)
K: Number of metal atoms per $m^2$ (for Cu=1.46×10$^{19}$ $m^2$)
$N_1$: Avogadro's number (6.022052×10$^{23}$ mol$^{-1}$)

The preparation of the novel supported catalysts to be used is preferably carried out with the aid of the pore impregnation method. A copper compound is dissolved in an amount of solvent which corresponds to the pore volume of the carrier, the carrier is impregnated with the solution and the impregnated catalyst is then dried for from 1 to 48, preferably from 12 to 24, hours at from 80 to 170° C., preferably from 100 to 150° C. The preferably used solvent is water. Alternatively to pore impregnation, impregnation can also be effected with an amount of solvent which is greater than the pore volume of the carrier (impregnation with supernatant solution). In addition the dried catalyst can be calcined for from 0.5 to 10, preferably from 1 to 3, hours, as a rule in an air current at from 200 to 600° C., preferably from 250 to 400° C.

Examples of suitable copper compounds are copper nitrate, copper halides, copper carbonate, copper carboxylates, copper acetylacetonate or copper amine complexes. An ammoniacal copper carbonate solution which is prepared by dissolving copper carbonate in aqueous ammonia solution is preferably used for the catalyst preparation.

The preparation of the unsupported catalysts to be used according to the invention is carried out, for example, by precipitation of a copper salt solution in the presence of the other catalyst components, preferably $TiO_2$, $Al_2O_3$, $ZrO_2$ or mixtures thereof, in a preferred embodiment the secondary components being present as powder in an aqueous suspension. The copper is precipitated from the copper salt solution in a manner known per se, preferably with sodium carbonate solution.

The precipitates which have separated out are filtered out, washed alkali-free and dried at from 50 to 150° C., preferably 120° C., and, if required, then calcined in general at from 200 to 400° C., in particular from 200 to 220° C.

In principle, all soluble Cu(I) and/or Cu(II) salts, for example sulfates, nitrates, chlorides, carbonates, acetates, oxalates or ammonium complexes, may be used as starting substances. Copper nitrate is particularly preferably used.

The dried powder obtained as described above is preferably molded to give tablets or similar moldings. Graphite, preferably in an amount of 3% by weight, based on the weight of the dry powder, is added as a tabletting aid for the molding process. If required, metallic copper powder is introduced as a further additive for the preparation of the catalyst, in addition to the powder described above and to graphite. Preferably from 5 to 40, in particular from 15 to 20% by weight, based on the weight of the dried powder described above, of metallic copper powder are added.

The tablet moldings are heated at from 300 to 600° C., in particular from 330 to 350° C., preferably for 2 hours. In comparison with the exclusive use of graphite as a tabletting aid in the conventional processes, this tabletting process permits particularly easy molding of the powder into tablets and gives catalysts which are chemically and mechanically very stable.

Before use as catalyst/halogen absorbers, the copper catalysts must be further reduced in order to convert the copper component into the metallic state. The reduction is carried out, for example, by passing a hydrogen-containing gas, preferably $H_2/N_2$ mixtures having $H_2$ contents of 50–100% by volume, at from 100–250° C., preferably 150–200° C., for 10–48, preferably 20–30, hours, over the copper catalyst already present in the reactor.

The removal of the halogen-containing impurities from the ester mixture with the copper-containing catalysts/halogen absorbents can be carried out both in the liquid phase and in the gas phase. The procedure is preferably carried out in the liquid phase. The removal of the hydrogen-containing impurities from the ester mixture can be carried out batchwise or continuously. Continuous operation is preferably employed.

In the removal of the halogen-containing impurities in the liquid phase in continuous operation, the copper-containing halogen absorbent is introduced, for example, into a tube reactor and activated as described above by treatment with a hydrogen-containing gas, and the ester mixture containing the halogen-containing impurities is passed over the catalyst at a liquid space velocity of 0.05–50 kg of ester mixture per 1 of catalyst per hour, at 50–250° C., preferably 100–200° C., particularly preferably 150–180° C., and at a pressure which is chosen so high that no gas phase can form, for example 1–100, preferably 1–10, particularly preferably 1–5, bar, either from bottom to top (liquid-phase procedure) or from top to bottom (trickle-bed procedure). The liquid-phase procedure is preferably employed. The concentration of the halogen-containing compounds in the purified ester mixture is in general less than 0.5 ppm, preferably less than 0.1 ppm, of Cl.

Starting materials of any desired origin which, owing to their preparation method, contain organic halogen compounds as impurities are suitable dialkyl adipates to be purified according to the invention, in particular esters of adipic acid with low molecular weight alcohols, for example with alcohols of 1 to 4 carbon atoms, or ester mixtures containing these.

However, an ester fraction as obtained
 a) by esterification of an aqueous dicarboxylic acid mixture which contains adipic acid, 6-hydroxycaproic acid and small amounts of 1,4-cyclohexanediols and which is obtained as a byproduct in the oxidation of cyclohexane to cyclohexanone/cyclohexanol with oxygen or oxygen-containing gases and by water extraction of the reactor mixture with a low molecular weight alcohol, preferably n-butanol, isobutanol or in particular methanol,
 b) removal of the excess alcohol and of the low boilers in a first distillation stage and
 c) separation of the bottom product in a second distillation stage into a fraction containing at least the major part of the cyclohexanediols and an ester fraction which is essentially free of 1,4-cyclohexanediols and is to be hydrogenated is preferably used as a starting material.

The preparation of this ester fraction is described in detail in WO 97/31882. It contains up to 1000, as a rule up to 100, and in particular less than 10, ppm of halogen-containing organic compounds, such as chlorinated cyclohexanes, especially monochlorocyclohexane, 1,2-dichlorocyclohexane, 1,3-dichlorocyclohexane and 1,4-dichlorocyclohexane, as impurities which cannot be separated off by distillation.

These organic halogen compounds are cleaved and absorbed over the copper catalysts to be used according to the invention, as a rule to less than 0.1 ppm, frequently less than the limit of detection. The hydrogenation of the dialkyl adipates freed from the organic halogen compounds or of the ester mixtures containing these is carried out in a manner known per se and with catalysts known per se. Hydrogenation conditions and catalysts are described in detail in WO 97/31882, so that this publication is hereby expressly incorporated by reference. The features of the process described in WO 97/31882 are essentially the following:

For a better understanding, the process for the preparation of hexanediol is illustrated according to FIG. 1, in which the individual process steps are divided into further stages, stages 2, 3, 4, 5, 6, 7 being essential to the process and it also being possible for stages 3 and 4 as well as 6 and 7 to be combined. Stages 8, 9, 10 and 11 are optional but may be useful for increasing the cost-efficiency of the process.

The dicarboxylic acid solution (DAS) is in general an aqueous solution containing from 20 to 80% of water. Since an esterification reaction is an equilibrium reaction, it is generally useful, particularly in the case of esterification with, for example, methanol, if any water present is removed before the reaction, especially if water cannot be removed, for example cannot be removed azeotropically, during the esterification reaction. The removal of water in stage 1 can be effected, for example, using a membrane system, or preferably by distillation apparatus, in which, at from 10 to 250° C., preferably from 20 to 200° C., particularly preferably from 30 to 200° C., and from 1 to 1500, particularly preferably from 5 to 1100, particularly preferably from 20 to 1000, mbar, water is separated off via the top and higher monocarboxylic acids, dicarboxylic acids and 1,4-cyclohexanediols via the bottom. The bottom temperature is preferably chosen so that the bottom product can be removed in liquid form. The water content in the bottom of the column may be from 0.01 to 10, preferably from 0.01 to 5, particularly preferably from 0.01 to 1% by weight.

The water can be separated off in such a way that the water is obtained predominantly acid-free, or the lower monocarboxylic acids contained in the DAS—essentially formic acid—can for the most part be distilled off with the water so that they do not bind any esterification alcohol in the esterification.

An alcohol of 1 to 10 carbon atoms is mixed with the carboxylic acid stream from stage 1, according to variant A alcohols of 1 to 3 carbon atoms, i.e. methanol, ethanol, propanol or isopropanol, preferably methanol, and according to variant B alcohols of 4 to 10, in particular 4 to 8, carbon atoms, particularly preferably n-butanol, isobutanol, n-pentanol and isopentanol.

The mixing ratio of alcohol to carboxylic acid stream (mass ratio) may be from 0.1 to 30, preferably from 0.2 to 20, particularly preferably from 0.5 to 10.

This mixture, in the form of a melt or solution, reaches the reactor of stage 2, in which the carboxylic acids are esterified with the alcohol. The esterification reaction can be carried out at from 50 to 400° C., preferably from 70 to 300° C., particularly preferably from 90 to 200° C. An external pressure can be applied, but the esterification is preferably carried out under the autogenous pressure of the reaction system. A stirred kettle or flow tube or a plurality thereof may be used as esterification apparatuses. The residence time required for the esterification is from 0.3 to 10, preferably from 0.5 to 5, hours. The esterification reaction can take place without the addition of a catalyst; however, a catalyst is preferably added in order to increase the reaction rate. Said catalyst may be homogeneously dissolved or a solid catalyst. Examples of homogeneous catalysts are sulfuric acid, phosphoric acid, hydrochloric acid, sulfonic acids, such as p-toluenesulfonic acid, heteropolyacids, such as tungstophosphoric acid, or Lewis acids, such as aluminum, vanadium, titanium or boron compounds. Mineral acids are preferred, in particular sulfuric acid. The weight ratio of homogeneous catalyst to carboxylic acid melt is as a rule from 0.0001 to 0.5, preferably from 0.001 to 0.3.

Suitable solid catalysts are acidic or superacidic materials, for example acidic and superacidic metal oxides, such as $SiO_2$, $Al_2O_3$, $SnO_2$ or $ZrO_2$, or sheet silicates or zeolites, all of which can be doped with mineral acid radicals, such as sulfate or phosphate, in order to enhance the acidity, or organic ion exchangers having sulfonic acid or carboxylic acid groups. The solid catalysts can be arranged as a fixed bed or used as a suspension.

The water formed in the reaction is advantageously removed continuously, for example by a membrane or by distillation.

The completeness of the conversion of the free carboxyl groups present in the carboxylic acid melt is determined by the acid number (mg KOH/g) measured after the reaction. Less any acid added as catalyst, it is from 0.01 to 50, preferably from 0.1 to 10. Not all carboxyl groups present in the system are present as esters of the alcohol used, and instead some may be present in the form of dimeric or oligomeric esters, for example with the OH end of the hydroxycaproic acid.

The esterification mixture is fed into stage 3, a membrane system or preferably a distillation column. If a dissolved acid was used as the catalyst for the esterification reaction, the esterification mixture is advantageously neutralized with a base, from 1 to 1.5 base equivalents being added per acid equivalent of the catalyst 1. As a rule, alkali metal or alkaline earth metal oxides, carbonates, hydroxides or alcoholates or amines, as such or dissolved in the esterification alcohol, are used as bases.

If a column is used in stage 3, the feed to the column is preferably effected between the top stream and the bottom stream. The excess esterification alcohol ROH, water and, for example, corresponding esters of formic acid, acetic acid and propionic acid are taken off via the top at from 1 to 1500, preferably from 20 to 1000, particularly preferably from 40 to 800, mbar and at from 0 to 150° C., preferably from 15 to 90° C., and in particular from 25 to 75° C. This stream can either be incinerated or can preferably be further worked up in stage 11.

An ester mixture which predominantly consists of the esters of the alcohol ROH used with dicarboxylic acids, such as adipic acid and glutaric acid, hydroxycarboxylic acids, such as 6-hydroxycaproic acid and 5-hydroxyvaleric acid, and of oligomers and free or esterified 1,4-cyclohexanediols is obtained as the bottom product. It may be useful to permit a residual content of water and/or alcohol ROH up to 10% each in the ester mixture. The bottom temperatures are from 70 to 250° C., preferably from 80 to 220° C., particularly preferably from 100 to 190° C.

The stream from stage 3, substantially freed from water and esterification alcohol ROH, is fed into stage 4. This is a distillation column in which the feed is generally effected between the low boiling components and the high boiling components. The column is operated at from 10 to 300° C., preferably from 20 to 270° C., particularly preferably from 30 to 250° C., and from 1 to 1000, preferably from 5 to 500, particularly preferably from 10 to 200, mbar.

According to variant A, i.e. the esterification with $C_1$- to $C_3$-alcohols, in particular methanol, the stream from stage 3 is now separated into a top fraction to be hydrogenated and a bottom fraction containing the 1,4-cyclohexanediols.

The top fraction consists predominantly of residual water and residual alcohol ROH, esters of the alcohol ROH with monocarboxylic acids, predominantly $C_3$- to $C_6$-monocarboxylic acids, esters with hydroxycarboxylic acids, such as 6-hydroxycaproic acid and 5-hydroxyvaleric acid, and especially the diesters with dicarboxylic acids, such as adipic acid, glutaric acid and succinic acid, and furthermore 1,2-cyclohexanediols, caprolactone and valerolactone.

The stated components can be separated off together via the top and fed to the hydrogenation (stage 5) or, in a further preferred embodiment, separated in the column into a top stream, which predominantly contains residual water and residual alcohol as well as the abovementioned esters of the $C_3$- to $C_5$-carboxylic acids, and a side stream which predominantly contains the abovementioned esters of the $C_6$-carboxylic acids and dicarboxylic acids, which then reach the hydrogenation.

The high boiling components of the stream from stage 4, predominantly consisting of 1,4-cyclohexanediols or the esters thereof, dimeric or oligomeric esters and undefined components of DCL, some of which are polymeric, are separated off via the stripping section of the column. These may be obtained together or in such a way that predominantly the 1,4-cyclohexanediols are separated off via a side stream of the column in the stripping section and the remainder via the bottom. The 1,4-cyclohexanediols thus obtained can be used, for example, as starting material for active ingredients. The high-boiling components, with or without the content of 1,4-cyclodiols, either can be incinerated or, in a preferred embodiment, passed to the transesterification in stage 8.

According to variant B, i.e. the esterification with $C_4$- to $C_{10}$-alcohols, in particular n-butanol or isobutanol, the stream from stage 3 can be separated in stage 4 into a top fraction containing the 1,4-cyclohexanediols, a side stream which predominantly contains the $C_6$-esters and passes to the hydrogenation and a bottom stream which contains high boiler and may pass to stage 8.

The top fraction consists predominantly of residual alcohol ROH, $C_1$- to $C_3$-monoesters of the alcohol ROH, valerolactone and 1,2- and 1,4-cyclohexanediols.

The side stream contains predominantly diesters of succinic acid, glutaric acid and adipic acid and monoesters of 5-hydroxyvaleric acid and 6-hydroxycaproic acid. This side stream can be removed either above or below the feed point of the column and fed into the hydrogenation (stage 5).

The bottom stream containing oligomeric esters and other high boilers can be either incinerated or advantageously fed to stage 8.

In a further embodiment, in stage 4 the $C_6$-esters are separated off together with the bottom stream and then, in a further column, either separated as a bottom product from the top fraction already described, which consists predominantly of residual alcohol ROH, $C_1$- to $C_3$-monoesters of the alcohol ROH, valerolactone and 1,2- and 1,4-cyclohexanediols, or separated as a top stream from the high boilers.

The fraction of stage 4 which is free or virtually free of 1,4-cyclohexanediols, either the total stream or the side stream containing mainly esters of $C_6$-acids, is passed into the hydrogenation stage 5.

The stages 3 and 4 can be combined, in particular when only small amounts are processed. For this purpose the $C_6$-ester stream can be obtained, for example in a fractional distillation carried out batchwise, once again without 1,4-cyclohexanediol entering the stream fed to the hydrogenation.

The hydrogenation is carried out catalytically, either in the gas phase or in the liquid phase. Suitable catalysts are in principle all homogeneous and heterogeneous catalysts suitable for hydrogenating carbonyl groups, such as metals, metal oxides, metal compounds or mixtures thereof. Examples of homogeneous catalysts are described, for example, in Houben-Weyl, Methoden der Organischen Chemie, volume IV/1c, Georg Thieme Verlag Stuttgart, 1980, pages 45–67) and examples of heterogeneous catalysts are described, for example, in Houben-Weyl, Methoden der Organischen Chemie, volume IV/1c, pages 16 to 26.

Catalysts which contain one or more of the elements from subgroups I and VI to VIII of the Period Table of Elements, preferably copper, chromium, molybdenum, manganese, rhenium, ruthenium, cobalt, nickel and palladium, particularly preferably copper, cobalt or rhenium, are preferably used.

The catalysts may consist of the active components alone or the active components may be applied to carriers. Suitable carrier materials are, for example, $Cr_2O_3$, $Al_2O_3$, $SiO_2$, $ZrO_2$, $ZnO_2$, BaO and MgO or mixtures thereof.

Catalysts as described in EP 0 552 463 are particularly preferred. These are catalysts which, in the oxidic form, have the composition $$Cu_aAl_bZr_cMn_dO_x$$

where a>0, b>0, c>0, d>0, a>b/2, b>a/4, a>c and a>d and x is the number of oxygen ions which is required to maintain the electrical neutrality per formula unit. These catalysts can be prepared, for example, according to EP 552 463 by precipitating sparingly soluble compounds from solutions which contain the corresponding metal ions in the form of their salts.

Suitable salts are, for example, halides, sulfates and nitrates. Suitable precipitating agents are all agents which lead to the formulation of such insoluble intermediates which can be converted into the oxides by thermal treatment. Particularly suitable intermediates are the hydroxides and carbonates or bicarbonates so that particularly preferably used precipitating agents are alkali metal carbonates or ammonium carbonate. The thermal treatment of the intermediates at from 500° C. to 1000° C. is important for the preparation of the catalysts. The BET surface area of the catalysts is from 10 to 150 $m^2/g$.

Heterogeneous catalysts which are either arranged as a fixed bed or used as a suspension are preferably used. If the hydrogenation is carried out in the gas phase and over a fixed-bed catalyst, in general temperatures of 150 to 300° C. and pressures of from 1 to 100, preferably from 15 to 70, bar are used. Hydrogen is used as a hydrogenating agent and carrier gas at least in an amount which is sufficient to ensure that starting materials, intermediates and products never become liquid during the reaction. The excess hydrogen is preferably circulated, it being possible to remove a small part as waste gas for removing inert substances, such as methane. One reactor or a plurality of reactors connected in series may be used.

If the hydrogenation is carried out in the liquid phase using a fixed-bed or suspended catalyst, it is in general effected at from 100 to 350° C., preferably from 120 to 300° C., and at from 30 to 350, preferably from 40 to 300, bar.

The hydrogenation can be carried out in one reactor or in a plurality of reactors connected in series. The hydrogenation in the liquid phase over a fixed bed can be carried out both by the trickle-bed procedure and by the liquid-phase procedure. In a preferred embodiment a plurality of reactors is used, the predominant part of the esters being hydrogenated in the first reactor and the first reactor preferably being operated with a liquid circulation for heat removal and the subsequent reactor or reactors preferably being operated without circulation for completion of the conversion.

The hydrogenation can be carried out batchwise but is preferably effected continuously.

The hydrogenation discharge consists essentially of 1,6-hexanediol and the alcohol ROH. Further components, especially if the total low-boiling stream of stage 4 was used according to the variant A are 1,5-pentanediol, 1,4-butanediol, 1,2-cyclohexanediols and small amounts of monoalcohols of 1 to 6 carbon atoms and water.

This hydrogenation discharge is separated in stage 6, which is, for example, a membrane system or preferably a distillation column, into the alcohol ROH, which additionally contains the major part of the further low-boiling components, and a stream which predominantly contains 1,6-hexanediol in addition to 1,5-pentanediol and the 1,2-cyclohexanediols. At from 10 to 1500, preferably from 30 to 1200, particularly preferably from 50 to 1000, mbar, top temperatures of from 0 to 120° C., preferably from 20 to 100° C., particularly preferably from 30 to 90° C., and bottom temperatures of from 100 to 270° C., preferably from 140 to 260° C., particularly preferably from 160 to 250° C., are established. The low-boiling stream can either be recycled directly to the esterification of stage 2 or transported to stage 8 or to stage 11.

The 1,6-hexanediol-containing stream is purified in a column in stage 7. 1,5-Pentanediol, possibly the 1,2-cyclohexanediols and any further low boilers are separated off via the top. If the 1,2-cyclohexanediols and/or 1,5-pentanediol are to be obtained as additional desired products they can be separated in a further column. Any high boilers present are removed via the bottom. 1,6-Hexanediol is removed from a side stream of the column with a purity of at least 99%. At from 1 to 1000, preferably from 5 to 800, particularly preferably from 20 to 500, mbar, top temperatures of from 50 to 200° C., preferably from 60 to 150° C., and bottom temperatures of from 130 to 270° C., preferably from 150 to 250° C., are established.

The novel process is described in more detail below with reference to the following examples but is in no way restricted thereby.

Preparation of Catalyst A:

An active carbon carrier in the form of 2–5 mm granules is impregnated with an ammoniacal copper carbonate solution which was prepared by dissolving copper carbonate in a 25% strength by weight aqueous ammonia solution, the volume of the impregnating solution corresponding to the pore volume of the amount of carrier used. The impregnated carrier is dried for 16 hours at 120° C. The catalyst thus prepared has a copper content, calculated as CuO, of 6.0% by weight, a surface area of 820 $m^2/g$, a porosity of 0.65 $cm^3/g$ and, after reduction, a copper surface area of 2.9 $m^2/g$.

Preparation of Catalyst B:

A zirconium dioxide carrier in the form of 3 mm extrudates is impregnated with an ammoniacal copper carbonate solution which was prepared by dissolving copper carbonate in a 25% strength by weight aqueous ammonia solution, the volume of the impregnating solution corresponding to the pore volume of the amount of carrier used. The impregnated carrier is dried for 16 hours at 120° C. and then calcined for 1 hour at 350° C. The catalyst thus prepared has a copper content, calculated as CuO, of 5.0% by weight, a surface area of 74 $m^2/g$, a porosity of 0.30 $cm^3/g$ and, after reduction, a copper surface area of 1.1 $m^2/g$.

Preparation of Catalyst C:

Catalyst C was prepared by precipitating a solution of copper nitrate with sodium carbonate solution. A suspension of $TiO_2$ in water was used as the initially taken mixture. The precipitate formed during the precipitation was filtered off, washed and dried at 120° C. The dried powder was calcined for two hours at 200° C. and then compressed with 3% of graphite and 20% of metallic copper powder to give 3 mm tablets. These tablets were heated for 2 hours at 330° C.

The catalyst thus prepared has a copper content, calculated as CuO, of 44.0% by weight, a surface area of 39 $m^2/g$, a porosity of 0.22 $cm^3/g$ and, after reduction, a copper surface area of 1.4 $cm^3/g$.

EXAMPLE 1 a) Removal of the Cl-containing impurities (stages 1 to 4 according to example in WO 97/31882)

Stage 1 (dewatering)

0.1 kg/h of dicarboxylic acid solution (consisting essentially of adipic acid, 6-hydroxycaproic acid, 1,4-cyclohexanediols, glutaric acid, 5-hydroxyvaleric acid, formic acid and water) was distilled continuously in a distillation apparatus (three-tray bubble tray column with external oil heating circulation, oil temperature 150° C., tray volume about 25 ml each, feed via the bubble tray) with an attached packed column (about 4 theoretical plates, no reflux at the top). 0.045 kg/h with a formic acid content in the water of about 3% was obtained as the top product. In the bottom stream (5.5 kg), the water content was about 0.4%.

Stage 2 (esterification):

5.5 kg/h of the bottom stream from stage 1 were reacted continuously with 8.3 kg/h of methanol and 14 g/h of sulfuric acid in a tube reactor (1 0.7 m, 0 1.8 cm, residence time 2.7 h). The acid number of the discharge without sulfuric acid was about 10 mg KOH/g.

Stage 3 (removal of excess alcohol and of water):

The esterification stream from stage 2 was distilled in a 20 cm packet column (1015 mbar, 65° C. top temperature, up to 125° C. bottom temperature). 7.0 kg were taken off via the top. 6,8 kg were obtained as bottom products.

Stage 4 (fractionation; 1,4-cyclohexanediol isolation):

The bottom stream from stage 3 was subjected to fractional distillation in a 50 cm packet column (1 mbar, 70–90° C. top temperature, up to 180° C. bottom temperature). The bottom product (1.9 kg) contained virtually all 1,4-cyclohexanediols.

0.6 kg was distilled off as light boilers (1,2-cyclohexanediols, valerolactone, methyl 5-hydroxyvalerate, dimethyl glutarate, dimethyl succinate, etc.). 4.3 kg were obtained as a fraction containing predominantly dimethyl adipate and methyl 6-hydroxycaproate.

A tube reactor was filled with 50 ml of catalyst A. The catalyst was first reduced by passing pure hydrogen at 180° C. for a period of 24 hours over the catalyst present in the reactor. The fraction according to stage 4, containing predominantly methyl adipate and methyl hydroxycaproate and having a Cl content of 0.7 ppm was then passed over the catalyst with a liquid space velocity of 0.5 kg of ester mixture per 1 of catalyst per hour at 170° C. and at 1 bar, from bottom to top (liquid phase procedure). The Cl content of the reactor discharge was below the limit of detection of 0.1 ppm. No catalyst components were detectable in the reactor discharge, i.e. the catalyst is absolutely chemically stable to the ester mixture. No change in the composition of the ester mixture before and after the removal of the Cl-containing impurities was detectable by GC analysis.

b) hydrogenation (stage 5)

b 27kg of the $C_6$-ester mixture originating from stage a) and freed from the Cl-containing impurities were hydrogenated continuously in a 25 ml reactor over a catalyst (catalyst: 70% by weight of Cuo, 25% by weight of ZnO, 5% by weight of $Al_2O_3$) which had been activated beforehand in a stream of hydrogen at 180° C. (hydrogenation conditions: feed 20 g/h, no circulation, 220 bar, 220° C.). The ester conversion was 99.5% over the entire duration of the experiment and the 1,6-hexanediol selectivity was 99%.

EXAMPLE 2

Example 1 was repeated, except that in stage a) the tube reactor was filled with 50 ml of catalyst B. The catalyst was first reduced by passing pure hydrogen at 180° C. for a period of 24 hours over the catalyst present in the reactor. The fraction according to Example 1 containing predominantly methyl adipate and methyl hydroxycaproate and having a Cl content of 0.7 ppm was passed over the catalyst at a liquid space velocity of 0.5 kg of ester mixture per 1 of catalyst per hour at 170° C. and at 1 bar, from bottom to top (liquid phase procedure). The Cl content of the reactor discharge was below the limit of detection of 0.1 ppm. No catalyst components were detectable in the reactor discharge, i.e. the catalyst is absolutely chemically stable to the ester mixture. No change in the composition of the ester mixture before and after the removal of the Cl-containing impurities was detectable by GC analysis. The hydrogenation results were the same as in Example 1.

COMPARATIVE EXAMPLE 3

The process was carried out similarly to Example 1 up to and including the hydrogenation, but without the halogen-containing $C_6$-ester mixture being passed over a copper-containing halogen absorbent before the hydrogenation, i.e. without stage a). At the beginning of the hydrogenation, the ester conversion was 99.5% and the selectivity 99%. However, after only 6.0 kg of the total of 27 kg of the $C_6$-ester mixture to be hydrogenated had been converted, the ester conversion had decreased to only 90% and the selectivity to 97% owing to the deactivation of the hydrogenation catalyst by the halogen-containing impurities.

EXAMPLE 4

Example 1 was repeated, except that in stage a), the tube reactor was filled with 50 ml of catalyst C. The catalyst was first reduced by passing pure hydrogen at 180° C. for a period of 24 hours over the catalyst present in the reactor. The fraction according to Example 1, containing predominantly methyl adipate and methyl hydroxycaproate and having a Cl content of 0.7 ppm was passed over the catalyst with a liquid space velocity of 0.5 kg of ester mixture per 1 of catalyst per hour at 150° C. and at 1 bar, from bottom to top (liquid phase procedure). The Cl content of the reactor discharge was below the limit of detection of 0.1 ppm. No catalyst components were detectable in the reactor discharge, i.e. the catalyst was absolutely chemically stable to the ester mixture. No change in the composition of the ester mixture before and after the removal of Cl-containing impurities was detectable by GC-analysis. The hydrogenation results were the same as in Example 1.

We claim:

1. A process for the preparation of hexanediol by hydrogenating dialkyl adipates or mixtures which contain a dialkyl adipate as the essential component and organic compounds as impurities, wherein, before the hydrogenation, the dialkyl adipates or the mixtures containing dialkyl adipates are passed at from 50 to 250° C. and from 1 to 100 bar over copper catalysts which have a copper content, calculated as CuO, of from 0.5 to 80% by weight, a surface area of from 5 to 1500 $m^2$/g, a porosity of from 0.05 to 1.5 $cm^3$/g and a copper surface area of from 0.1 to 20 $m^2$/g, in order to remove the organic halogen compounds.

2. A process as claimed in claim 1, wherein copper catalysts which have a copper content, calculated as CuO, of from 2 to 60% by weight, a surface area of from 10 to 1000 $m^2$/g, a porosity of from 0.1 to 0.8 $cm^3$/g and a specific copper surface area of from 0.5 to 10.0 $m^2$/g are used.

3. A process as claimed in claim 1, wherein $TiO_2$-containing unsupported copper catalysts which have a copper content, calculated as CuO, of from 20 to 60% by weight, a surface area of from 10 to 150 $m^2$/g, a porosity of from 0.1 to 0.5 $cm^3$/g and a specific copper surface area of from 0.5 to 3.0 $m^2$/g are used.

4. A process as claimed in claim 1 wherein $ZrO_2$-supported copper catalysts which have a copper content, calculated as CuO, of from 2 to 8% by weight, a surface area of from 50 to 150 $m^2$/g, a porosity of from 0.2 to 0.4 $cm^3$/g and a specific copper surface area of from 1.0 to 3.0 $m^2$/g are used.

5. A process as claimed in claim 1, wherein active carbon-supported copper catalysts which have a copper content, calculated as CuO, of from 2 to 8% by weight, a surface area of from 500 to 1000 m²/g, a porosity of from 0.5 to 0.8 cm³/g and a specific copper surface area of from 1.0 to 5.0 m²/g are used.

6. A process as claimed in claim 1, wherein the halogen-containing impurities are removed in the liquid phase in continuous operation with a liquid space velocity of 0.05–50 kg of ester mixture per 1 of catalyst per hour at 50–250° C. and at 1–100 bar.

7. A process as claimed in claim 1, wherein the halogen-containing impurities are removed in the liquid phase in continuous operation with a liquid space velocity of 0.1–10 kg of ester mixture per 1 of catalyst per hour at 100–200° C. and at 1–10 bar.

8. A process as claimed in claim 1, wherein the halogen-containing impurities are removed in the liquid phase in continuous operation with a liquid space velocity of 0.2–1.0 kg of ester mixture per 1 of catalyst per hour at 150–180° C. and at 1–5 bar.

9. A process as claimed in claim 1, wherein the starting material used is an ester fraction as obtained (a) by esterification of an aqueous dicarboxylic acid mixture, which contains adipic acid, 6-hydroxycaproic acid and small amounts of 1,4-cyclohexanediols and which is obtained as a byproduct in the oxidation of cyclohexane to cyclohexanone/cyclohexanol with oxygen or oxygen-containing gases and by water extraction of the reaction mixture, with a low molecular weight alcohol, (b) removal of the excess alcohol and of the low boilers in a first distillation stage and (c) separation of the bottom product in a second distillation into a fraction containing at least the major part of the cyclohexanediols and an ester fraction which is essentially free of 1,4-cyclohexanediols and is to be hydrogenated.

10. A process as claimed in claim 1, wherein the content of organic halogen compounds is reduced to less than 0.1 ppm.

* * * * *